(12) United States Patent
Gollakota et al.

(10) Patent No.: US 11,660,046 B2
(45) Date of Patent: *May 30, 2023

(54) SYSTEMS AND METHODS OF IDENTIFYING MOTION OF A SUBJECT

(71) Applicant: University of Washington, Seattle, WA (US)

(72) Inventors: Shyamnath Gollakota, Seattle, WA (US); Rajalakshmi Nandakumar, Seattle, WA (US); Nathaniel F. Watson, Seattle, WA (US)

(73) Assignee: University of Washington, Seattle, WA (US)

( * ) Notice: Subject to any disclaimer, the term of this patent is extended or adjusted under 35 U.S.C. 154(b) by 348 days.

This patent is subject to a terminal disclaimer.

(21) Appl. No.: 16/836,530

(22) Filed: Mar. 31, 2020

(65) Prior Publication Data

US 2020/0297273 A1  Sep. 24, 2020

Related U.S. Application Data

(63) Continuation of application No. 15/532,981, filed as application No. PCT/US2015/053288 on Sep. 30, 2015, now Pat. No. 10,638,972.

(Continued)

(51) Int. Cl.
*A61B 5/00* (2006.01)
*A61B 5/113* (2006.01)
(Continued)

(52) U.S. Cl.
CPC .......... *A61B 5/4818* (2013.01); *A61B 5/0816* (2013.01); *A61B 5/1126* (2013.01); *A61B 5/1135* (2013.01); *A61B 5/742* (2013.01)

(58) Field of Classification Search
CPC ..... A61B 5/4818; A61B 5/742; A61B 5/0816; A61B 5/1126; A61B 5/1135; A61B 5/0826

See application file for complete search history.

(56) References Cited

U.S. PATENT DOCUMENTS 4,483,345 A  11/1984 Niwa
4,958,638 A  9/1990 Sharpe et al.
(Continued)

FOREIGN PATENT DOCUMENTS

CN  101489478 A  7/2009
CN  103167828 A  6/2013
(Continued)

OTHER PUBLICATIONS

Examination Report dated Jul. 8, 2021 in European Patent Application No. 15867802.9, 5 pages.

(Continued)

*Primary Examiner* — Chu Chuan Liu
(74) *Attorney, Agent, or Firm* — Perkins Coie LLP

(57) ABSTRACT

Systems and methods of identifying medical disorders in one or more subjects are disclosed herein. In one embodiment, sound is transmitted toward a subject and at least a portion of the sound reflected by the subject and is acquired as echo data. The acquired echo data is used to generate a motion waveform having a plurality of peaks detected therein. At least a portion of the plurality of peaks may be indicative of movement of the subject. One or more medical disorders in the subject can be identified based on, for example, time durations and/or amplitude changes between peaks detected in the motion waveform.

19 Claims, 7 Drawing Sheets

Related U.S. Application Data

(60) Provisional application No. 62/152,519, filed on Apr. 24, 2015, provisional application No. 62/089,130, filed on Dec. 8, 2014.

(51) Int. Cl.
*A61B 5/08* (2006.01)
*A61B 5/11* (2006.01)

(56) References Cited

U.S. PATENT DOCUMENTS

| | | | |
|---|---|---|---|
| 6,062,216 | A | 5/2000 | Corn et al. |
| 6,083,173 | A | 7/2000 | Grant et al. |
| 6,171,258 | B1 | 1/2001 | Karakasoglu |
| 8,562,526 | B2 | 10/2013 | Heneghan et al. |
| 10,638,972 | B2 | 5/2020 | Gollakota et al. |
| 2005/0038353 | A1* | 2/2005 | Rapoport ............ A61B 5/4818 128/204.23 |
| 2005/0171443 | A1 | 8/2005 | Gorenberg et al. |
| 2010/0172689 | A1 | 7/2010 | Tamano |
| 2011/0208060 | A1 | 8/2011 | Haase et al. |
| 2011/0237948 | A1 | 9/2011 | Corn et al. |
| 2012/0172689 | A1 | 7/2012 | Albert et al. |
| 2013/0155031 | A1 | 6/2013 | Dahl |
| 2013/0289401 | A1 | 10/2013 | Colbaugh et al. |
| 2014/0058256 | A1 | 2/2014 | De et al. |
| 2014/0163343 | A1 | 6/2014 | Heneghan et al. |
| 2020/0297273 | A1 | 9/2020 | Gollakota et al. |

FOREIGN PATENT DOCUMENTS

| | | |
|---|---|---|
| JP | 2009538720 A | 11/2009 |
| JP | 2013072865 A | 4/2013 |
| JP | 2013543741 A | 12/2013 |

OTHER PUBLICATIONS

Abeyratne, U.R. et al., "Obstructive sleep apnea screening by integrating snore feature classes," Physiological Measurement 34 (2013) pp. 99-121.
Al-Abed, M.A. et al., "Detection of Airway Occlusion in Simulated Obstructive Sleep Apnea/Hypopnea using Ultrasound: an In Vitro Study," IEEE, Aug. 31-Sep. 4, 2010, 4 pages.
Alqassim, S. et al., "Sleep Apnea Monitoring Using Mobile Phones," American University of Sharjah, Oct. 2012, 5 pages.
Catalano, Frank, "University of Washington develops app to detect signs of sleep apnea at home," accessed at < http://www.geekwire.com/2015/university-of-washington-develops-app-to-detect-signs-of-sleep-apnea-at-home/> 2015.
Centers for Disease Control and Prevention, Morbidity and Mortality Weekly Report, vol. 60, No. 8, Mar. 4, 2011, 36 pages.
Chen, Z. et al., "Unobtrusive Sleep Monitoring using Smartphones," 2013 7th Int. Conf. on Pervasive Computing Tech, for Healthcare and Workshops, 8 pages.
Deutsch, P.A. et al., "Cost-Effectiveness of Split-Night Polysomnography and Home Studies in the Evaluation of Obstructive Sleep Apnea Syndrome," JCSM, vol. 2, No. 2, 2006, 9 pages.
Examination Reoprt dated Oct. 1, 2019 for Australian Patent Application No. 2015361171, 3 pages.
Extended European Search Report dated Jun. 27, 2018 in European Patent Application No. 15867802.9, 9 pages.
Final Office Action dated Sep. 11, 2019 in U.S. Appl. No. 15/532,981 for Gollakota, filed Jun. 2, 2017, 18 pages.
Fitbit Official Site for Activity Trackers & More, https://www.fitbit.com/home, retrieved Mar. 6, 2019, 5 pages.
Flemons, W.W. et al., "Access to Diagnosis and Treatment of Patients with Suspected Sleep Apnea," Am J Respir Crit Care Med,, vol. 169, pp. 2004, 668-672.
Fox, N.A. et al., "An Evaluation of a Non-contact Biomotion Sensor with Actimetry," IEEE, Aug. 23-26, 2007, 5 pages.
Golpe, R. et al., "Home Sleep Studies in the Assessment of Sleep Apnea/Hypopnea Syndrome," Clinical Investigations, 6 pages.
Hao, T. et al., "iSleep: Unobtrusive Sleep Quality Monitoring using Smartphones," SenSys 2013, 14 pages.
Hao, T. et al., "RunBuddy: A Smartphone System for Running Rhythm Monitoring," UBICOMP Sep. 7-11, 2015, 12 pages.
International Search Report and Written Opinion dated Jun. 30, 2016 in International Patent Application No. PCT/US2015/053288, 8 pages.
Kay, M. et al., "Lullaby: A Capture & Access System for Understanding the Sleep Environment," UbiComp, 2012, 10 pages.
Kushida, C.A. et al., "Clinical Guidelines for the Manual Titration of Positive Airway Pressure in Patients with Obstructive Sleep Apnea," JCSM, vol. 4, No. 2, 2008, 15 pages.
Lahav, Y. et al., "Tongue Base Ultrasound: A Diagnostic Tool for Predicting Obstructive Sleep Apnea," Annals of Otology, Rhinology & Laryngology 118(3), 2009, pp. 179-184.
Markowitz, Maury, et al."Continuous-wave radar," accessed Jun. 2, 2017 at <https://en.wikipedia.org/wiki/Continuous-wave_radar?oldid=669841251>.
Masa, J.F. et al., "Effectiveness of home respiratory polygraphy for the diagnosis of sleep apnoea and hypopnea syndrome," Thorax, 2011, pp. 567-573.
Meng, A.Z., "SleepMinder: An Innovative Contact-Free Device for the Estimation of the Apnoea-Hypopnoea Index," IEEE, Sep. 2-6, 2009, 4 pages.
Min, J.K. et al., "Toss 'N' Turn: Smartphone as Sleep and Sleep Quality Detector," Human-Computer Interaction Institute, 10 pages.
Nandakumar, Rajalakshmi, et al. "Contactless Sleep Apnea Detection on Smartphones," May 2015.
Non-Final Office Action dated Mar. 1, 2019 in U.S. Appl. No. 15/532,981 for Gollakota et al., filed Jun. 2, 2017, 15 pages.
Norman, M.B. et al., "Validation of the Sonomat: A Contactless Monitoring System Used for the Diagnosis of Sleep Disordered Breathing," Sleep, vol. 37, No. 9, 2014, 11 pages.
Nose Breathe Mouthpiece: Health Benefits of Nasal Breathing, "Introducing Nose Breathe: 28,000 reasons to smile every single day," https://www.nosebreathe.com, retrieved Mar. 6, 2019, 4 pages.
Notice of Allowance dated Jan. 2, 2020 in in U.S. Appl. No. 15/532,981 for Gollakota et al., filed Jun. 2, 2017, 15 pages.
Pascual, A., Sleep Apnea Monitor, https://itunes.apple.com/gb/app/sleep-apnea-monitor/id464587229?mt=8, retrieved Mar. 6, 2019, 4 pages.
Patwari, N. et al., "Breathfinding: A Wireless Network that Monitors and Locates Breathing in a Home," Feb. 15, 2013, 10 pages.
Patwari, N. et al., "Monitoring Breathing via Signal Strength in Wireless Networks," IEEE Transactions on Mobile Computing, 14 pages.
Rahman, T. et al., "BodyBeat: A Mobile System for Sensing Non-Speech Body Sounds," MobiSys Jun. 16-19, 2014, 12 pages.
Ralston, T.S. et al., "Real-time Through-wall Imaging Using an Ultrawideband Multiple-Input Multiple-Output (NIMO) Phased Array Radar System," IEEE, 2010, 8 pages.
Ren, Yanzhi et al., "Poster: Hearing Your Breathing: Fine-grained Sleep Monitoring Using Smartphones," MobiCom, Sep. 7-11, 2014, 3 pages.
Se Dong Min et al., "Noncontact Respiration Rate Measurement System Using an Ultrasonic Proximity Sensor," IEEE Sensors Journal, vol. 10, No. 11, Nov. 2, 2010, pp. 1732-1739.
Shouldice, R.B. et al., "Real Time Breathing Rate Estimation From a Non Contact Biosensor," IEEE, Aug. 31, 2010-Sep. 4, 2010, 4 pages.
Shu, C.C. et al., "The Use of Sub-Mental Ultrasonography for Identifying Patients with Severe Obstructive Sleep Apnea," PLOS One, vol. 8, Issue 5, 7 pages.
Sleep Access, http://sleepaccess.com, retrieved Mar. 6, 2019, 1 page.
Sleep as Android, https://sites.google.com/site/sleepasandroid, retriever Mar. 6, 2019, 2 pages.
SleepIQ Labs, https://bamlabs.com, retrieved Mar. 6, 2019, 1 page.
Snuza, Baby Monitors, https://www.snuza.com, retrieved Mar. 6, 2019 5 pages.

(56) References Cited

OTHER PUBLICATIONS

Strohl, K.P. et al., "Drowsy Driving and Automobile Crashes," Nat. Highway Traffic Safety Admin. 1998, 39 pages.
Vernier.com, Respiration Monitor Belt, https://www.vernier.com/products/sensors/respiration-monitors/rmb, retrieved Mar. 11, 2019, 8 pages.
Visvanathan, A. et al., "Increasing Clinical Presence of Mobile Communication Technology: Avoiding the Pitfalls," Telemedicine and e-Health, Oct. 2011, 6 pages.
Wu, H.Y. et al., "Eulerian Video Magnification for Revealing Subtle Changes in the World," MIT, retrieved Mar. 8, 2019, 9 pages.
Young, T. et al., "The Occurrence of Sleep-Disordered Breathing Among Middle-Aged Adults," The New England Journal of Medicine, Apr. 29, 1993, 6 pages.
Zito, D. et al., "A 90nm CMOS SoC UWB Pulse Radar for Respiratory Rate Monitoring," ISSCC 2011, Session 2, 2 pages.
First Examination Report dated Jul. 14, 2021 in New Zealand Application No. 732493, 7 pages.
Examination Report dated Jan. 27, 2022 in New Zealand Patent Application No. 732493, 5 pages.
Examination Report dated May 23, 2022 in New Zealand Patent Application No. 732493, 4 pages.

\* cited by examiner

SYSTEMS AND METHODS OF IDENTIFYING MOTION OF A SUBJECT

CROSS-REFERENCE TO RELATED APPLICATION(S)

This application claims the benefit of pending U.S. Provisional Application No. 62/089,130, filed Dec. 8, 2014, and U.S. Provisional Application No. 62/152,519, filed Apr. 24, 2015. The foregoing applications are incorporated herein by reference in their entireties.

TECHNICAL FIELD

The present technology relates generally to identifying motion of a portion of a subject's body and associated methods and systems. In particular, several embodiments are directed to methods of tracking motion of a subject's body for use in identifying sleep apnea, although these or similar embodiments may be used in identifying chronic obstructive pulmonary disease (COPD), monitoring infant respiration and/or detecting other movements of the subject.

BACKGROUND

Sleep apnea is a common medical disorder that occurs when breathing is disrupted during sleep. Sleep apnea is estimated to affect nearly 1 in 20 American adults and is linked to attention deficit/hyperactivity disorder, high blood pressure, diabetes, heart attack, stroke and increased motor vehicle accidents. Sleep apnea is commonly diagnosed in a dedicated sleep clinic that administers polysomnography tests. In a polysomnography test, a trained technician attaches and monitors sensors on the subject for the duration of the subject's sleep over a single night. Polysomnography tests, however, can be expensive, time-consuming and labor-intensive, and subjects may have to wait several weeks to receive a polysomnography test due to long wait lists. Alternatively, a home sleep apnea test (HSAT) may be performed using a portable recording system in a subject's home, typically during a single night's sleep. During an HSAT, the subject still typically wears several measurement instruments connected to the portable recording system. Such home tests can also be problematic. For example, improper attachment of one or more of the measurement instruments may affect the accuracy of a home sleep test.

DETAILED DESCRIPTION

Figure 1:
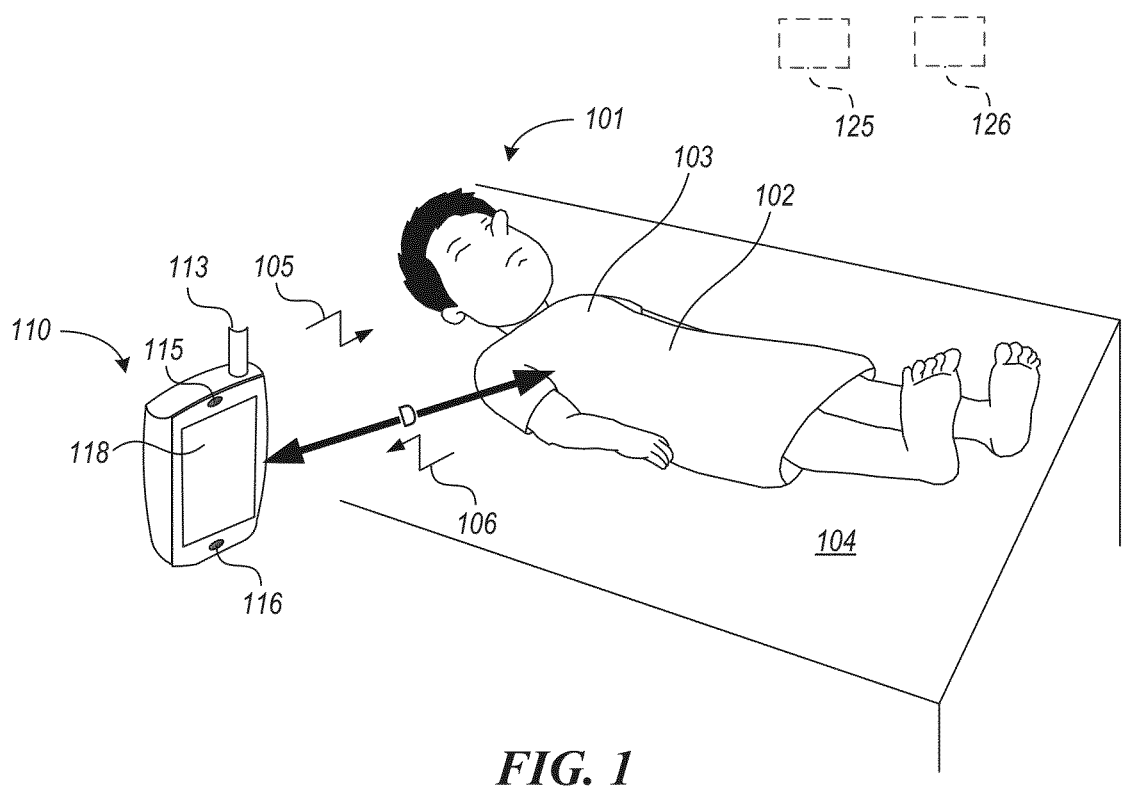
FIG. 1 is a schematic diagram of a device shown adjacent a human subject and configured in accordance with embodiments of the present technology.

The present technology relates generally to identifying motion of a portion of a subject's body and associated methods and systems. In one embodiment of the present technology, for example, a method of identifying sleep apnea events in a subject includes transmitting sound energy toward the subject using a first transducer (e.g., a loudspeaker) and receiving echoes from the subject corresponding to the transmitted sound energy using a second transducer (e.g., a microphone). Electrical signals corresponding to the echoes are used to generate a waveform and a plurality of peaks can be detected in the waveform. Individual peaks in the waveform can have corresponding amplitudes indicative of a breathing motion of the subject. An indication of a sleep apnea event can be output for each occurrence of a period of time between successive individual peaks in the waveform exceeding a predetermined threshold time. In some aspects, transmitting the sound energy comprises emitting a plurality of audio chirps from the first transducer that linearly sweep from a first frequency (e.g., about 18 kHz) to a second, higher frequency (e.g., about 20 kHz or higher) over a predetermined time duration (e.g., between about 5 ms and about 15 ms, about 10.75 ms).

In another embodiment of the present technology, a method of operating an electronic device to monitor movements of a subject proximate the electronic device includes emitting a plurality of audio sweep signals toward the subject from a loudspeaker operatively coupled to the electronic device. The individual audio sweep signals linearly sweep from a first frequency less than 20 kHz (e.g., about 18 kHz) to a second, higher frequency (e.g., about 20 kHz or higher) over a predetermined time duration (e.g., between about 5 ms and about 15 ms, about 10.75 ms). The method further includes acquiring audio data at a microphone operatively coupled to the electronic device. The audio data can include echo signals corresponding to individual audio sweep signals backscattered by the subject toward the microphone. The acquired audio data is processed to generate a motion waveform. One or more peaks detected in the motion waveform are indicative of movements of the subject. The method also includes outputting an indication of movement of the subject (e.g., motion of the subject's chest or abdomen) based one or more of the detected peaks. In some aspects, for example, at least a portion of the plurality of the audio sweep signals comprise frequency-modulated continuous-wave sound signals. In some aspects, the method also includes calculating a plurality of frequency domain representations of the echo signals that are calculated over a time period lasting a predetermined multiple (e.g., 10) of the predetermined time duration (e.g., 10.75 ms) of the individual audio sweep signals. In some aspects, the method can include determining a frequency shift in the individual frequency domain representations relative to the first frequency.

In yet another embodiment of the present technology, a computer program product comprising computer usable program code executable to perform operations for outputting an indication of a sleep apnea event in a subject. The operations include transmitting a plurality of chirp signals to a first transducer (e.g., a loudspeaker) operatively coupled to a mobile device. The individual chirp signals linearly sweep from a first frequency less than 20 kHz (e.g., 10 kHz, 16 kHz, 18 kHz) to a second, higher frequency (e.g., 19 kHz, 20 kHz, 22 kHz, 30 kHz) over a predetermined time duration (e.g., 5 ms, 10 ms, 20 ms, 30 ms). The operations further include acquiring echo data from a second transducer (e.g., a microphone) operatively coupled to the mobile device. The echo data includes data corresponding to individual chirp signals reflected by the subject toward the second transducer. The operations also include demodulating the acquired echo data to obtain a motion signal indicative of respiratory motion of the subject, and detecting one or more amplitude peaks in the motion signal. The operations further comprise outputting an indication of a sleep apnea event if a period of time between successive individual amplitude peaks in the motion signal exceeds a predetermined threshold time. In some aspects, the operations can further include repeating the transmitting and acquiring for a predetermined number of transmit/acquisition cycles. In some aspects, the demodulating the acquired echo data can include performing a single Fourier transform over the predetermined number of transmit/acquisition cycles.

These and other aspects of the present disclosure are described in greater detail below. Certain details are set forth in the following description and in FIGS. 1-8C to provide a thorough understanding of various embodiments of the disclosure. Other details describing well-known systems and methods often associated with motion tracking and/or identification have not been set forth in the following disclosure to avoid unnecessarily obscuring the description of the various embodiments.

In the Figures, identical reference numbers identify identical, or at least generally similar, elements. To facilitate the discussion of any particular element, the most significant digit or digits of any reference number refers to the Figure in which that element is first introduced. For example, element 110 is first introduced and discussed with reference to FIG. 1. Many of the details, dimensions, angles and other features shown in the Figures are merely illustrative of particular embodiments of the disclosed technology. Accordingly, other embodiments can have other details, dimensions, angles and features without departing from the spirit or scope of the disclosure. In addition, those of ordinary skill in the art will appreciate that further embodiments of the invention can be practiced without several of the details described below.

Devices and Methods for Detecting Motion of a Subject

FIG. 1 is a schematic diagram of a device 110 configured in accordance with embodiments of the present technology. The device 110 is positioned near a human subject 101 lying on a bed 104 such that the subject's abdomen 102 and chest 103 are approximately a distance D (e.g., 1 meter) from the device 110. A first transducer 115 (e.g., a loudspeaker) is configured to emit acoustic energy (e.g., sounds between about 20 Hz and 20 kHz or higher), including sound 105. A second transducer 116 (e.g., a microphone) is configured to receive acoustic energy including reflected sound 106 received from the subject's body 102. A communication link 113 (e.g., an antenna) communicatively couples the device 110 to a communication network (e.g., the Internet, a cellular telecommunications network, a WiFi network). A user interface 118 is configured to receive input from the subject 101 and/or another user, and is further configured to provide visual output to the subject 101 and/or another user. In the illustrated embodiment of FIG. 1, the user interface 118 comprises a touchscreen display. In some embodiments, the user interface 118 may include, for example, one or more keypads, touchpads, touchscreens, trackballs, mice and/or additional user interface devices or systems (e.g., a voice input/output system). Moreover, in some embodiments, one or more additional speakers 125 and one or more additional microphones 126 may optionally be positioned near the bed 104 separate from the device 110, and communicatively coupled to the device 110 via the communication link 113 and/or another communication link. In some other embodiments, the device 110 may include one or more additional speakers and/or microphones (not shown).

In the illustrated embodiment of FIG. 1, the device 110 is a depicted as a mobile phone (e.g., a smartphone). In other embodiments, however, the device 110 may comprise any suitable electronic device such as, for example, a tablet, a personal display assistant, a laptop computer, a desktop computer, a set top box and/or another electronic device configured to transmit and receive sound. In certain embodiments, the device 110 may comprise a component of one or more systems and/or devices (e.g., a baby monitor, a security system, an automobile entertainment system, a stereo system, a home intercom system, a clock radio). Moreover, in the illustrated embodiment of FIG. 1, the subject 101 (e.g., a human adult, a human child, an animal) is shown lying asleep on the bed 104 (e.g., a bed in the subject's bedroom, a bed in a medical facility, a bed in a sleep laboratory). In other embodiments, however, the subject 101 may be awake and/or upright. In some embodiments, the device 110 may be configured to emit the sound 105 toward and receive the reflected sound 106 from one or more additional subjects (not shown).

In operation, the device 110 generates audio signals—including, for example, frequency modulated continuous wave (FMCW) audio signals—that sweep from a first frequency (e.g., about 18 kHz) to a second frequency (e.g., about 20 kHz). The first transducer 115 transmits the generated audio signals as the sound 105 toward the subject 101. A portion of the sound 105 is reflected and/or backscattered by the subject's chest 103 and/or abdomen 102 toward the second transducer 116 as the reflected sound 106. The second transducer 116 receives the reflected sound 106 and converts it into one or more reflected audio signals. As discussed in further detail below in reference to FIGS. 3-5 and 6B, the device 110 can be configured to detect peaks in the reflected audio signals that correspond to movements of the subject's chest 103 and/or abdomen 102. And as discussed in further detail below in reference to FIGS. 3 and 7-8C, the device 110 can be further configured to identify and/or disambiguate one or more apnea events (e.g., a central apnea event, an obstructive apnea event, a hypopnea event) in the subject based on the detected peaks. In some embodiments, the device 110 is also configured to identify movements of the subject's chest 103 and/or abdomen 102 that correspond to movements associated with chronic obstructive pulmonary disease (COPD) or infant respiration.

As those of ordinary skill in the art will appreciate, conventional approaches to the identification of sleep disorders and/or other medical disorders can include overnight stays at a medical facility using dedicated (and often expensive) medical equipment. One conventional approach is a clinical polysomnography (PSG) test, which is traditionally used to diagnose sleep apnea and other sleep disorders. A PSG is typically conducted overnight in a sleep laboratory where a trained technician monitors a subject's sleeping patterns. The technician attaches a number of sensors to the subject including, for example, a chest and abdomen belt to measure breathing movements, a nasal pressure transducer and thermistor, a snore microphone, a pulse oximeter to measure oxygen saturation, a movement sensor on each leg to detect movements, a sensor to determine muscular tone of the chin, sensors to monitor eye movements and/or EEG sensors to measure brain activity. The sensors are all connected using wires and the technician monitors the live data stream from the sensors throughout the sleep duration.

One metric used for sleep apnea identification is the Apnea-Hypopnea Index (AHI), which represents a rate at which apnea and hypopnea events occur during a sleep period. Physicians can classify the sleep apnea level using AHI values. For example, AHI values ranging from 0 to 5 are typically classified as no-apnea; AHI values between 5 and 15 are typically classified as mild-apnea; AHI values between 15 and 30 are typically classified as moderate-apnea and AHIs of 30 or higher are typically classified as severe apnea. The apnea-hypopnea index can computed as follows:

$$AHI = \frac{\text{\# central apnea} + \text{\# hypopnea} + \text{\# obstructive apnea}}{\text{total sleep time}} \quad (1)$$

In equation 1 above, central apnea, hypopnea, and obstructive apnea correspond to the parameters that are tracked during a typical PSG study. To compute these parameters, the sensor data collected during the sleep period (typically 6-8 hours) is split into 30-second intervals called epochs. The scoring process of analyzing these epochs may involve two steps. A first step is staging, which identifies whether the subject is awake or asleep in each epoch and if asleep, what sleep stage is present. This is achieved by examining the brain activity obtained from the EEG sensors and the chin tone and eye movement sensor information. At the end of this step, each epoch can be marked as being in either a wake or sleep stage. A second step involves identifying the number of central apnea, hypopnea, and obstructive apnea events, using American Academy of Sleep Medicine (AASM) guidelines. For example, a central apnea event can occur when the subject holds her breath for a non-negligible duration. A hypopnea event can occur, for example, when the subject's chest motion drops by more than 30% with an accompanying 4% oxygen desaturation. A hypopnea may also be determined by presence of a 3% desaturation or an "arousal" (abrupt frequency change) on the EEG. An obstructive apnea event can occur, for example, when the subject makes an increased effort to pull air into the lungs but only a minimal amount of air reaches the lungs due to blockage.

As those of ordinary skill in the art will appreciate, polysomnography procedures for sensor data collection and processing can be both labor and time intensive. For example, it may take about an hour for the technician to fit each subject with sensors typically employed in a PSG measurement. Further, throughout a sleep duration (e.g., an eight-hour sleep duration), the technician may continue to monitor the sensors and confirm the sensors remain properly attached to the subject's body. Sensor data is typically processed manually to tag every epoch with the sleep apnea events. Moreover, while an HSAT may be performed in a subject's home, the test still requires attaching sensors to the subject that include, for example, chest and abdomen belts, nasal pressure sensors, transducer and thermistors, EKG sensors, pulse oximetry sensors, and/or pulse arterial tonometry sensors. Home testing can have a high failure rate (e.g., 33%) due to signal loss resulting from detachment of wires and cables In contrast to these conventional approaches outlined above, the disclosed technology is expected to be considerably less labor intensive and time consuming. For example, the disclosed techniques for detecting movement of at least a portion of the subject's body (e.g., a chest, an abdomen) use sound waves without sensors in contact with the subject. The disclosed technology accordingly eliminates the use of wires or cables that may cause test failure due to improper attachment and/or signal loss. The disclosed technology is also expected provide a benefit of identifying one or more medical conditions (e.g., sleep apnea. COPD) while the subject sleeps or rests in his or her own bed and uses a relatively inexpensive device (e.g., the subject's own smartphone or another personal electronic device, a computer, an off-the-shelf mobile device, etc.). As a result, the disclosed technology can reduce or eliminate the time and/or expenses associated with a technician monitoring the subject during an entire sleep duration. The disclosed technology is further expected to allow concurrent monitoring and movement detection of multiple subjects via a single device.

In some embodiments, the disclosed technology can also be utilized in the identification of a potential presence of COPD in a subject. As those of ordinary skill in the art will appreciate, COPD is a chronic inflammatory lung disease that causes obstructed airflow from the lungs. Symptoms of COPD can include breathing difficulty, coughing, sputum production and wheezing. COPD exacerbations can involve an acute worsening of the patient's condition and can be a major cause of morbidity and mortality associated with this disease. Increased respiratory frequency and reduced tidal volume are common physiological characteristics of COPD exacerbations. The disclosed technology can assess the frequency and depth of breathing in real time to identify COPD exacerbations in the early stages. Such early detections and corresponding treatment are expected to help prevent worsening of this condition.

Suitable Systems

The following discussion provides a brief, general description of a suitable environment in which the technology may be implemented. Although not required, aspects of the technology are described in the general context of computer-executable instructions, such as routines executed by a general-purpose computer. Aspects of the technology can be embodied in a special purpose computer or data processor that is specifically programmed, configured, or constructed to perform one or more of the computer-executable instructions explained in detail herein. Aspects of the technology can also be practiced in distributed computing environments where tasks or modules are performed by remote processing devices, which are linked through a communication network (e.g., a wireless communication network, a wired communication network, a cellular communication network, the Internet, a short-range radio network (e.g., via Bluetooth)). In a distributed computing environment, program modules may be located in both local and remote memory storage devices.

Computer-implemented instructions, data structures, screen displays, and other data under aspects of the technology may be stored or distributed on computer-readable storage media, including magnetically or optically readable computer disks, as microcode on semiconductor memory, nanotechnology memory, organic or optical memory, or other portable and/or non-transitory data storage media. In some embodiments, aspects of the technology may be distributed over the Internet or over other networks (e.g. a Bluetooth network) on a propagated signal on a propagation medium (e.g., an electromagnetic wave(s), a sound wave) over a period of time, or may be provided on any analog or digital network (packet switched, circuit switched, or other scheme).

Figure 2:
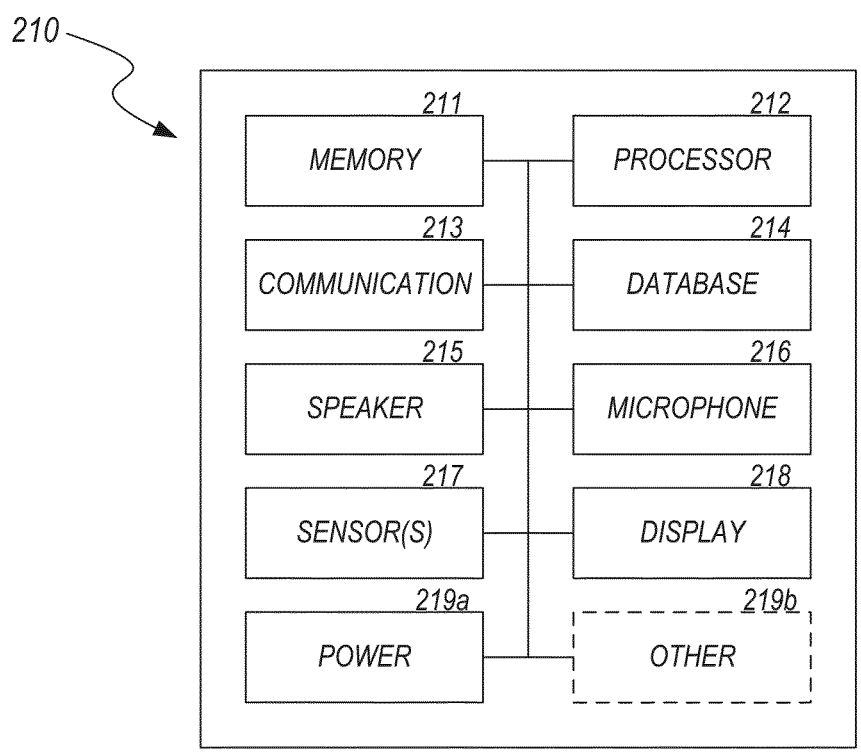
FIG. 2 is a block diagram of a system configured in accordance with embodiments of the present technology.

FIG. 2 is a block diagram of a system 210 configured in accordance with embodiments of the present technology. The system 210 includes several components including memory 211 (e.g., one or more computer readable storage modules, components, devices). In some embodiments, the memory 211 comprises one or more applications installed and/or operating on a computer and/or a mobile device (e.g., the device 110 of FIG. 1, a tablet, a smartphone, a PDA, a portable media player, or other "off-the-shelf" mobile device). The memory 211 can also be configured to store information (e.g., audio data, subject information or profiles, environmental data, data collected from one or more sensors, media files). A processor 212 (e.g., one or more processors or distributed processing elements) is coupled to the memory 211 and configured to execute operations and/or instructions stored thereon.

A speaker 215 (e.g., the first transducer 115 and/or the speaker 125 of FIG. 1) operatively coupled to the processor is configured to receive audio signals from the processor 212 and/or one or more other components of the system 210 and output the audio signals as sound (e.g., the sound 105 of FIG. 1). In some embodiments, the speaker 215 includes a conventional dynamic loudspeaker disposed in a mobile device (e.g., a smartphone or tablet). In some embodiments, the speaker 215 includes an earphone transducer and/or a standalone loudspeaker. In other embodiments, the speaker 215 includes a suitable transducer configured to output acoustic energy in at least a portion of the human audible frequency spectrum (e.g., between about 20 Hz and 20 kHz).

A microphone 216 (e.g., the second transducer 116 and/or the microphone 126 of FIG. 1) operatively coupled to the processor is configured to receive sound, convert the sound into one or more electrical audio signals and transmit the electrical audio signals to the memory 211 and/or the processor 212. In some embodiments, the microphone 216 includes a microphone disposed in a mobile device (e.g., a smartphone or tablet). In some embodiments, the microphone 216 is located on an earphone and/or along a cable connected to one or more earphones. In other embodiments, the microphone 216 includes another suitable transducer configured to receive acoustic energy in at least a portion of the human audible spectrum. Moreover, in some embodiments, the speaker 215 and the microphone 216 are spaced apart by a distance (e.g., 2 cm or greater, between about 2 cm and 10 cm, between 4 cm and 8 cm, or at least about 6 cm). In other embodiments, however, the speaker 215 is immediately adjacent the microphone 216. In certain embodiments, a single transducer can transmit sound energy and receive sound energy. In further embodiments, the speaker 215 and/or the microphone 216 comprise one or more additional transducers to form one or more transducer array(s). The transducer array(s) can be configured to transmit and/or receive beamformed audio signals.

Communication components 213 (e.g., a wired communication link and/or a wireless communication link (e.g., Bluetooth. Wi-Fi, infrared and/or another wireless radio transmission network)) communicatively couple the system 210 to one or more communications networks (e.g., a telecommunications network, the Internet, a WiFi network, a local area network, a wide area network, a Bluetooth network). A database 214 is configured to store data (e.g., audio signals and data acquired from a subject, equations, filters) used in the identification of movements of a subject. One or more sensors 217 are configured to provide additional data for use in motion detection and/or identification. The one or more sensors 217 may include, for example, one or more ECG sensors, blood pressure monitors, galvanometers, accelerometers, thermometers, hygrometers, blood pressure sensors, altimeters, gyroscopes, magnetometers, proximity sensors, barometers and/or hall effect sensors.

One or more displays 218 (e.g., the user interface 118 of FIG. 1) provide video output and/or graphical representations of data acquired and processed by the system 210. A power supply 219a (e.g., a power cable connected to a building power system, one or more batteries and/or capacitors) provides electrical power to components of the system 210. In embodiments that include one or more batteries, the power supply 219a can be configured to recharge, for example, via a power cable, inductive charging, and/or another suitable recharging method. Furthermore, in some embodiments, the system 210 optionally includes one or more other components 219b (e.g., one or more microphones, cameras, Global Positioning System (GPS) sensors, Near Field Communication (NFC) sensors).

As explained in further detail below in reference to FIGS. 3-8C, the system 210 is configured to transmit sound toward a subject and receive sound reflected by the subject. The transmitted and received sound can be used by the system 210 to detect movement of the subject and identify one or more medical conditions (e.g., sleep apnea, COPD) in the subject. In some embodiments, for example, the memory 211 includes instructions for generating audio signals (e.g., FMCW audio signals that sweep from about 18 kHz to about 20 kHz or higher) and providing the generated audio signals to the speaker 215. The speaker 215 transmits the audio signals as sound (e.g., acoustic energy comprising one or more waveforms) and directs at least a portion of the transmitted sound toward a subject (e.g., the subject 101 of FIG. 1) proximate the speaker 215. A portion of the sound is reflected or backscattered toward the microphone 216, which converts the sound into electrical audio signals. The memory 211 can further include instructions for processing the electrical audio signals to detect motion of the subject (e.g., movement of the subject's chest and/or abdomen), to disambiguate between periodic motion (e.g., respiratory motion) and non-periodic motion, and to identify one or more medical conditions (e.g., an apnea event, COPD) in the subject based on the detected motion of the subject. In some embodiments, an indication of the identified medical condition can be output to the display 218 and/or can be transmitted via the communication component 213 to a medical professional (e.g., a nurse, a doctor). In certain embodiments, the system 210 can be configured to determine baseline breathing information (e.g., breathing frequency) about a subject and store the baseline breathing information. The baseline breathing information can be compared to subsequent breathing measurements to identify a respiratory disorder.

Suitable Methods

Figure 3:
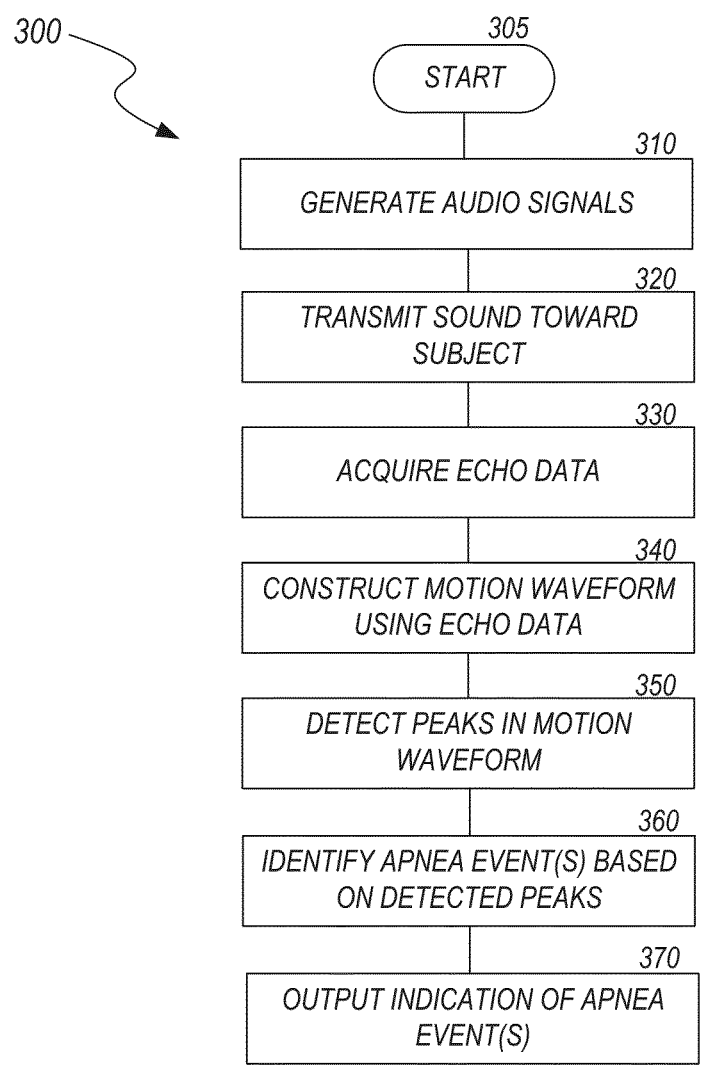
FIG. 3 is a flow diagram of a process configured in accordance with an embodiment of the present technology.
Figure 4A:
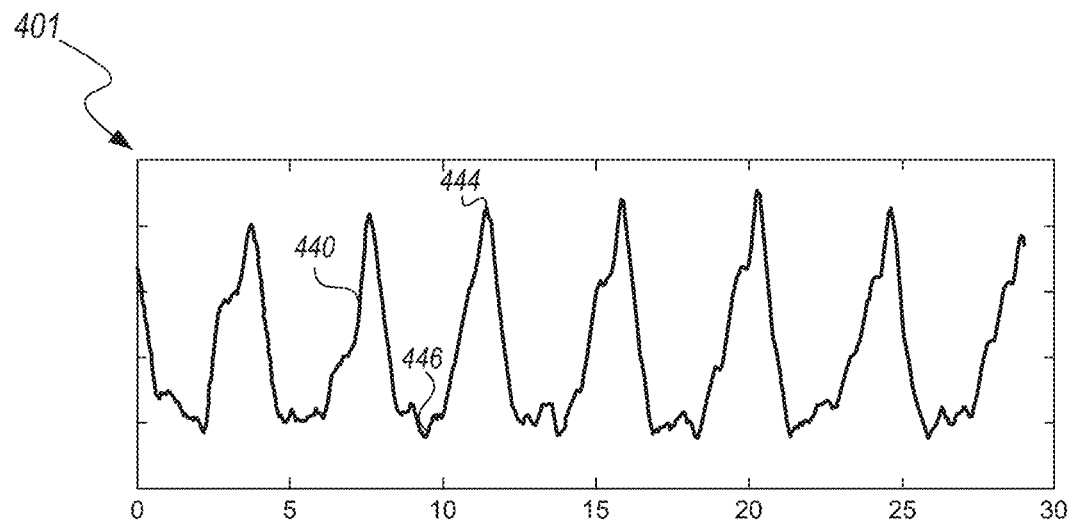
FIG. 4A is a graph depicting a motion waveform acquired in accordance with an embodiment of the present technology.
Figure 4B:
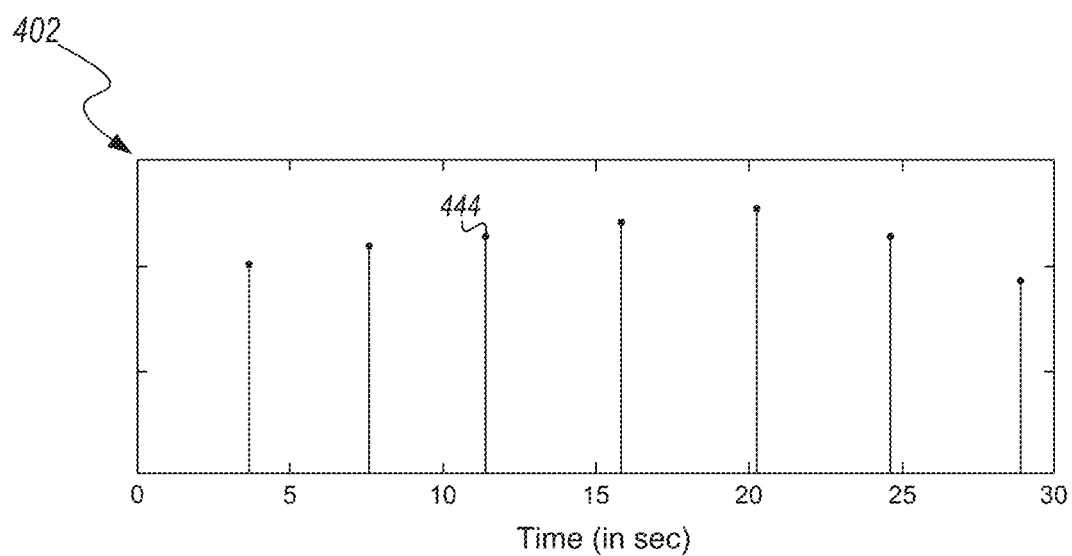
FIG. 4B is a graph depicting peaks detected in a motion waveform in accordance with an embodiment of the present technology.

FIG. 3 is a flow diagram of a process 300 configured to detect an apnea event in accordance with an embodiment of the present technology. FIG. 4A is a graph 401 depicting an example of a motion waveform acquired by the process 300 in accordance with an embodiment of the present technology. FIG. 4B is a graph 402 depicting peaks detected in the motion waveform of FIG. 4A in accordance with an embodiment of the present technology.

Referring first to FIG. 3, the process 300 can comprise a set of instructions stored on memory (e.g., the memory 211 of FIG. 2) and executed by one or more processors (e.g., the processor 212 of FIG. 2). In some embodiments, the process 300 comprises one or more smartphone applications stored on a device (e.g., the device 110 of FIG. 1). The process 300 begins at block 305 after the device and/or transducers are positioned proximate a subject (e.g., 1 m away from the subject, between about 0.5 m and 10 m from the subject, between about 1 m and 5 m from the subject) and/or the subject's bed (e.g., the bed 104 of the subject 101 of FIG. 1). At block 305, the process 300 monitors the subject to determine whether the subject is asleep. In some embodiments, for example, the process 300 may monitor movements of the subject to detect random, non-periodic motions that the process 300 determines are not associated with breathing motion of the subject. For example, if the process 300 detects a predetermined number of occurrences (e.g., two, three, four or higher) of non-periodic motion within a predetermined time period, (e.g., 5 minutes, 10 minutes, 20 minutes), the process 300 may determine that the subject is awake for the duration of the predetermined time period. Conversely, if the process 300 does not detect the predetermined number of occurrences of non-periodic motion within the predetermined time period, the process 300 may determine that the subject is asleep during the entire predetermined time period. Collectively, a sum of a plurality of predetermined time periods that do not include the predetermined number of occurrences of detected non-periodic motion may form the basis of an overall measurement of sleep time during a session or test. Such an overall measurement of sleep time may be used, for example, in the denominator of equation 1 discussed above. In some embodiments, the process 300 is configured to wait a predetermined amount of time (e.g., one hour, two hours, four hours) before proceeding to the next step.

In some embodiments, the process 300 can detect an orientation of the device and, based on this detection, prompt a user to take corrective action. For example, the process 300 may provide more accurate detection if a predetermined side of a measurement device (e.g., a front facing portion of the device 110 shown in FIG. 1) is oriented at a predetermined orientation relative to the subject. In some embodiments, for example, it may be preferable to have a side of the measurement device on which the speaker is located or most closely positioned to be oriented toward the subject. In embodiments in which the speaker and a microphone are not on the same side of the measurement device, however, it may be desirable to acquire audio from the subject if a side of the measurement device on which a microphone is positioned is facing upright and/or substantially oriented toward the subject.

The process 300 can be configured to determine an orientation of the measurement device using, for example, one or more sensing mechanisms (e.g., one or more gyroscopes, accelerometers, compass sensors). In some embodiments, for example, the one or more sensing mechanisms include one or more of the sensors 217 discussed above with reference to FIG. 2. In some embodiments, the process 300 can generate one or more audible and/or visible indications instructing the subject and/or another user to take a corrective action based on the determined orientation. The corrective actions may include, for example, moving and/or orienting the measurement device toward the location of the subject. In some embodiments, the process 300 may not proceed until one or more corrective actions are detected. Alternatively, the one or more audible and/or visible indications may persist while other blocks are executed in process 300. In some embodiments, the process 300 can be configured to adjust detection thresholds based on a detected orientation.

At block 310, the process 300 generates one or more audio signals. In some embodiments, the audio signals include FMCW signals having a sawtooth waveform that includes a plurality of sweep audio signals or "chirps" that linearly sweep from a first frequency to a second, higher frequency. In some embodiments, the chirps sweep from a first audible frequency (e.g., about 18 kHz) to a second audible frequency (e.g., 20 kHz or higher). As those of ordinary skill in the art will appreciate, the frequency spectrum of a typical human ear ranges from 20 Hz to about 20 kHz, and many transducers are configured for playback over this spectrum. As humans age, however, the sensitivity of the ears to higher frequencies typically diminishes such that sounds having frequencies greater than about 18 kHz are effectively inaudible for a typical adult human. Accordingly, selecting the first and second audible frequencies to have a frequency equal to or greater than about 18 kHz allows for transmission of sound over a conventional loudspeaker configured for playback over the human audible frequency range while not disturbing most adults as they sleep. In other embodiments, the chirps sweep from a first audible frequency (e.g., 18 kHz) to a second inaudible frequency (e.g., a frequency greater than about 20 kHz and less than about 48 kHz, a frequency between about 22 kHz and about 44 kHz). In further embodiments, the chirps sweep between two frequencies outside the human audible range (e.g., greater than about 20 kHz and less than about 48 kHz). Moreover, in some embodiments, the process 300 generates audio signals comprising FMCW signals having a sine waveform, a triangle waveform and/or a square waveform. In other embodiments, the process 300 generates audio signals comprising pulse-modulated waveforms. In some embodiments, the process 300 generates audio signals using another suitable modulation method.

At block 320, the process 300 provides the generated audio signals to a transducer (e.g., the first transducer 115 of FIG. 1 and/or the speaker 215 of FIG. 2) configured to convert the audio signals to acoustic energy (e.g., the sound 105 of FIG. 1) and further configured to direct at least a portion of the acoustic energy toward the subject. At block 330, the process 300 acquires echo data from a microphone (e.g., the second transducer 116 of FIG. 1 and/or the microphone 216 of FIG. 2) or another transducer. The acquired echo data includes data corresponding to a portion of the sound transmitted toward the subject and reflected or backscattered toward the microphone and converted by the microphone to electrical signals.

Referring now to FIGS. 3, 4A and 4B together, at block 340 the process 300 constructs a motion waveform using the echo data. The process 300 analyzes the generated audio signals and the received echo data and detects frequency shifts therebetween that are indicative of movement of a portion of the subject's body (e.g., the subject's chest and/or abdomen). As explained in further detail below in reference to FIGS. 5A, 5B and 6, the frequency shifts can be used to generate the motion waveform as a function of time. One example of a motion waveform constructed by the process 300 at block 340 is shown in the graph 401 of FIG. 4A. The graph 401 includes a motion waveform 440 having a plurality of peaks 444 and a plurality of valleys or nulls 446.

At block 350, the process 300 detects one or more of the peaks 444 in the waveform 440 of FIG. 4A. The graph 402 of FIG. 4B shows one example of the peaks 444 detected by the process 300. Additional aspects of construction of a motion waveform and detection of the peaks in the waveform are described below in reference to FIG. 6.

At block 360, the process 300 analyzes the peaks (e.g., the peaks 444 of FIGS. 4A and 4B) detected in the motion waveform (e.g., the waveform 440 of FIG. 4A) to identify one or more sleep apnea events. For example, if an amplitude of a particular peak in the waveform is less than or equal to a predetermined threshold amplitude, the process 300 may determine that the particular peak corresponds to a hypopnea event in the subject. If, for example, successive peaks in the waveform are separated by a predetermined time (e.g., 10 seconds or greater), the process 300 may determine that the peak separation corresponds to a central apnea event. Further, if the process 300 detects a spike or a predetermined increase (e.g., 50%) in an amplitude between successive peaks, the process 300 may determine that the peak increase corresponds to an obstructive apnea event.

In some embodiments, the process 300 may compare a frequency of the detected peaks to a predetermined breathing frequency (e.g., a prior measurement of the patient's breathing frequency). The process 300 may further determine a possible presence of a COPD exacerbation in the subject if the frequency of the detected peaks is greater than or equal to a predetermined percentage (e.g., between about 105% and about 125%, or about 115%) of the predetermined breathing frequency. In some embodiments, the predetermined breathing frequency generally corresponds to a measured breathing frequency determined in a first portion or duration of a test, such as a predetermined period of time during a sleep measurement (e.g., an initial 30 minutes of the sleep measurement). The process 300 can use the measured breathing frequency as the subject's baseline breathing frequency. In other embodiments, however, the process 300 may use other predetermined percentages (e.g., about 130% or higher) and/or other predetermined periods of time (e.g., between about 15 minutes and about 30 minutes, between about 30 minutes and about 60 minutes, between about 60 minutes and about 120 minutes).

At block 370, the process 300 outputs an indication of one or more of the apnea events. In some embodiments, for example, the process 300 may store one or more indications of apnea events in a memory or database (e.g., the memory 211 and/or the database 214 of FIG. 2). In some embodiments, the process 300 may output an indication of one or more apnea events to a display (e.g., the user interface 118 of FIG. 1 and/or the display 218 of FIG. 2).

Figure 5A:
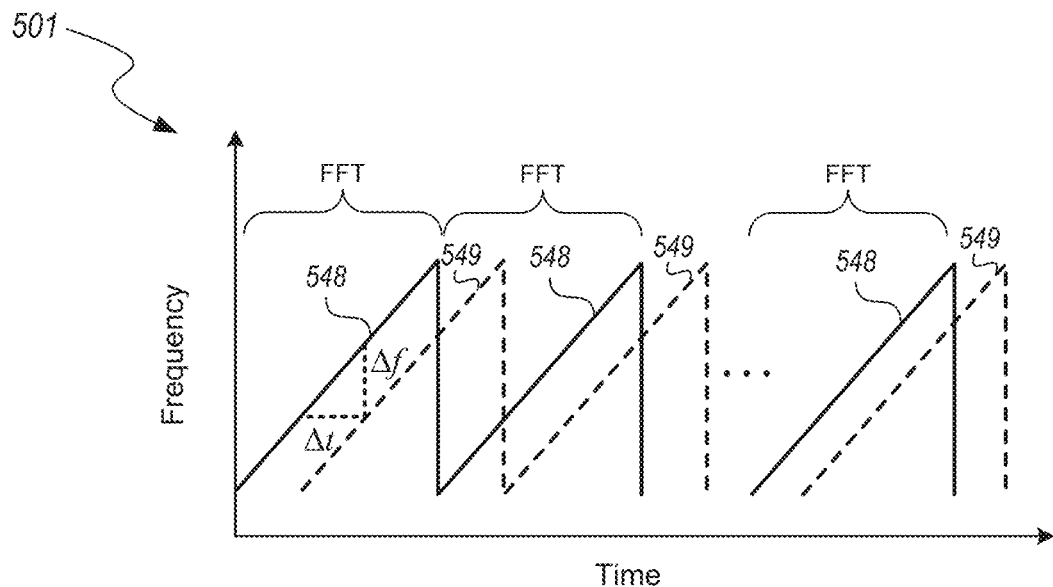
FIG. 5A is a graph depicting a prior art method of acquiring data.
Figure 5B:
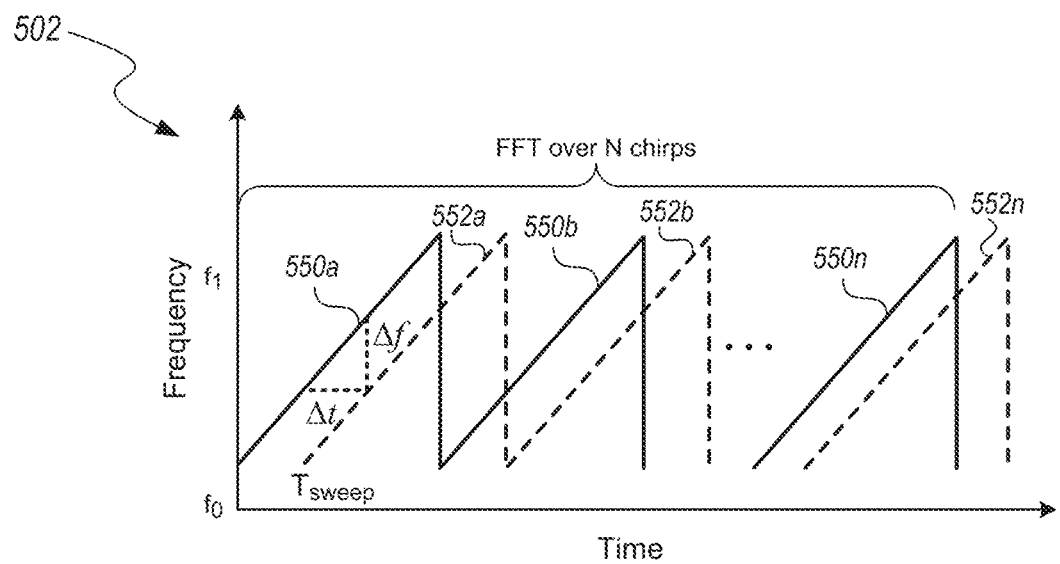
FIG. 5B is a graph depicting a method of acquiring data in accordance with an embodiment of the present technology.

FIG. 5A is a graph 501 depicting a conventional data acquisition approach in accordance with the prior art. FIG. 5B is a graph 502 depicting a method of acquiring data in accordance with an embodiment of the present technology. Referring first to FIG. 5A, the graph 501 includes a plurality of transmit signals 548 and a plurality of corresponding received signals 549. A fast fourier transform (FFT) is computed for each transmit/receive cycle.

Referring next to FIG. 5B, the graph 502 includes a plurality of transmitted signals 550 (identified individually as a first transmitted signal 550a, a second transmitted signal 550b, and an nth transmitted signal 550n) and a plurality of corresponding reflected signals 552 (identified individually as a first reflected signal 552a, a second reflected signal 552b, and an nth reflected signal 552n). The plurality of transmitted signals 552 comprise FMCW signals that linearly sweep between a first frequency $f_0$ (e.g., 18 kHz) and a second, higher frequency $f_1$ (e.g., 20 kHz or higher) over a time $T_{sweep}$ (e.g., between about 5 ms and about 15 ms, between about 10 ms and about 11 ms or about 10.75 ms).

The individual transmitted signals 550 are emitted from a loudspeaker (e.g., the first transducer 115 of FIG. 1) and a corresponding one of the reflected signals is received at a microphone (e.g., the second transducer 116 of FIG. 2) a period of time. For example, the first transmitted signal 550a is emitted from a loudspeaker and the corresponding first reflected signal 552a is received a time delay Δt later. The time delay Δt is given by:

$$\Delta t = \frac{2d}{V_{sound}} \quad (2)$$

in which d is the distance between the loudspeaker and the subject and $V_{sound}$ (i.e., approximately 340 m/s at sea level). Since the transmitted frequency increases linearly in time, time delays in the reflected signals translate to frequency shifts in comparison to the transmitted signals. The frequency shift Δf between individual transmitted signals and the corresponding reflected signals is given by the following:

$$\Delta f = \frac{f_1 - f_0}{T_{sweep}} \Delta t \quad (3)$$

With multiple reflectors at different distances from the receiver, their reflections translate to different frequency shifts in the signal. An FMCW receiver can extract all these frequency shifts (or demodulate the reflected signals) by performing a Fourier transform over one or more chirp durations. The chirp duration, $T_{sweep}$, is selected so that the reflections from all points within an operational distance (e.g., the distance D of FIG. 1) preferably start arriving before the chirp ends. In one particular embodiment, for example, the operational distance is approximately 1 meter, and a chirp duration of $T_{sweep}$ 10.75 ms is selected. The act of breathing creates minute chest and abdomen motion that can be captured by monitoring a corresponding bin in the Fourier transform as a function of time. One challenge, however, is that breathing movements are relatively small and thus may cause a very small frequency shift. A 2 cm breathing displacement, for example, may result in an 11.7 Hz frequency shift. Given a speed of sound of 340 m/s, a 48 kHz sampling rate translates to a resolution of 0.71 cm per sample. Further, a 10.7 ms chirp duration corresponds to 512 samples. With 18-20 kHz FMCW chirps, each sample corresponds to a 3.9 Hz frequency shift. Thus, a displacement of 0.71 cm can translate to a 3.9 Hz change in the frequency domain. Consequentially, a 2 cm breathing movement can create an 11.7 Hz frequency shift.

A frequency shift of 11.7 Hz can present a challenge because at a distance of 1 m and with a chirp duration of 10.75 ms, the width of each FFT bin is 93.75 Hz, which is much greater than the frequency shifts created due to breathing. To extract the minute frequency shifts created by breathing motion, an FFT is computed over an integer number of chirp durations as shown in FIG. 5B. This is in contrast to a traditional FMCW receiver that computes a Fourier transform over the duration of a single FMCW chirp as shown, for example in FIG. 5A. Computing an FFT over N chirps decreases a width of each FFT bin by a factor of N. In one embodiment, an FFT computed over ten chirps results in an FFT bin width of 9.37 Hz, allowing the capture of the 11.7 Hz frequency shifts resulting from the breathing movements.

Figure 6:
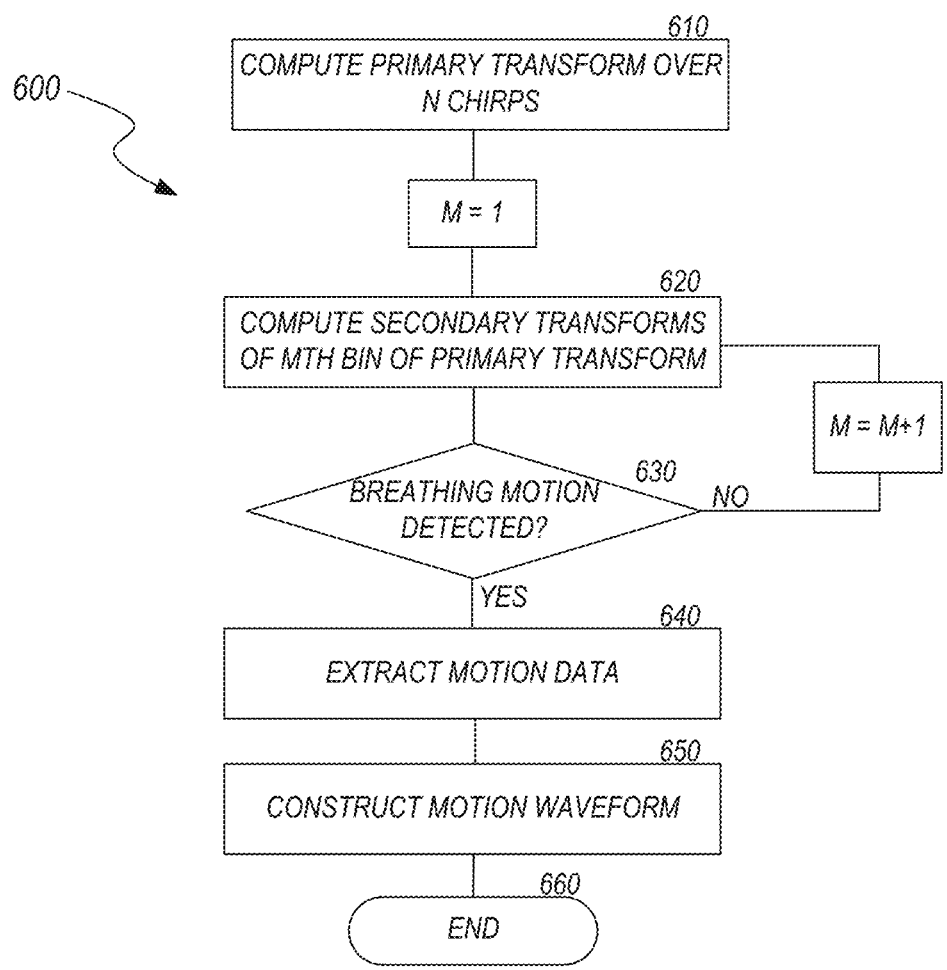
FIG. 6 is a flow diagram of a process configured in accordance with an embodiment of the present technology.

FIG. 6 is a flow diagram of a process 600 configured to identify motion in accordance with an embodiment of the present technology. The process 600 begins at block 610 with monitoring a plurality of transmit/receive cycles as described above in reference to FIG. 5B. The process 600 receives a plurality of reflected signals (e.g., the reflected signals 552 of FIG. 5) and computes a plurality of primary frequency transforms over a predetermined number N (e.g., 5, 10, 20, 40, 50) of chirps or transmit/receive cycles. As those of ordinary skill in the art will appreciate, a frequency transform converts and/or demodulates a signal from a first domain (e.g., a time domain) to a frequency domain. The primary transforms computed by the process 600 at block 610 represent frequency spectra of the reflected signals in a plurality of frequency bins. Each bin represents a discrete portion (e.g., about 1 Hz to about 100 Hz, about 5 Hz to about 50 Hz, about 8 Hz to about 12 Hz, about 9 Hz to about 10 Hz) of the frequency spectrum of the reflected signals. In some embodiments, for example, the process 600 computes a plurality of 5120-point FFTs over every series of 10 reflected signals received by the process 600. In one particular embodiment, for example, each bin of the primary transforms has a bandwidth of approximately 9.37 Hz.

At block 620, the process 600 computes a secondary frequency transform (e.g., an FFT) of an individual bin of each the primary transforms computed at block 610 over a predetermined time duration (e.g., 5 s, 10 s, 30 s, 60 s, 5 minutes, 10 minutes). When the process 600 initially proceeds to block 620, an index value m is set to 1. Accordingly, the process 600 performs an FFT of the $1^{st}$ bin of a plurality of the primary transforms as a function of time. In some embodiments, for example, the process 600 computes a 24,000-point FFT of the $1^{st}$ bins of a plurality of primary transforms over time duration of 30 seconds.

At decision block 630, the process 600 analyzes the secondary transform calculated at block 620 to determine whether the second transform includes one or more peaks associated with breathing frequencies. In some embodiments, for example, the process 600 analyzes the secondary transform from block 620 to determine if any peaks are detected between about 0.1 Hz or about 0.5 Hz (e.g., between about 0.2 Hz and about 0.3 Hz), which is a range that includes typical human breathing frequencies. If no peaks are detected at or near these frequency values, then the process 600 returns to block 620 and adds 1 to the index value m (i.e., m+1). The process 600 computes a new secondary transform at block 620 at the next bin m of the primary transforms over a predetermined period of time. The process 600 continues to iteratively compute secondary transforms until the process 600 detects peaks corresponding to breathing frequencies and/or until a predetermined value of m (e.g., 58, 60, 100, 200) is reached. If the process 600 detects a peak between about 0.1 Hz and about 0.5 Hz, the process 600 stores the index m corresponding to the bin number in which the peak is detected as $m_{peak}$, and proceeds to block 640.

At block 640, the process 600 extracts motion data from the reflected audio signals. In some embodiments, the process 600 continues to compute a plurality of the primary transforms of the reflected audio and compute a secondary transform of bin $m_{peak}$ of the primary transforms as a function of time. The process 600 can also compute a distance D between a measurement device (e.g., the device 110 of FIG. 1) and the subject using the $m_{peak}$ index obtained by the process 600 at block 640. For example, if the bandwidth of each bin is approximately 9.37 Hz. and bin index $m_{peak}$ obtained at block 630 is 58 (i.e., breathing motion detected in the $58^{th}$ bin of the primary transform of block 610), the resulting frequency shift caused by movement of the subject is approximately 1,087 Hz (9.37 Hz*58*2). Using equation 2 above, the time delay can be obtained as approximately 5.8 ms, which corresponds to a distance of about 1 m from the subject.

At block 650, the process 600 constructs a motion waveform (e.g. the motion waveform 440 of FIG. 4A) of movement of the subject's chest and/or abdomen as a function of time using the secondary transform computed at block 640. At block 660, the process 600 ends.

Figure 7:
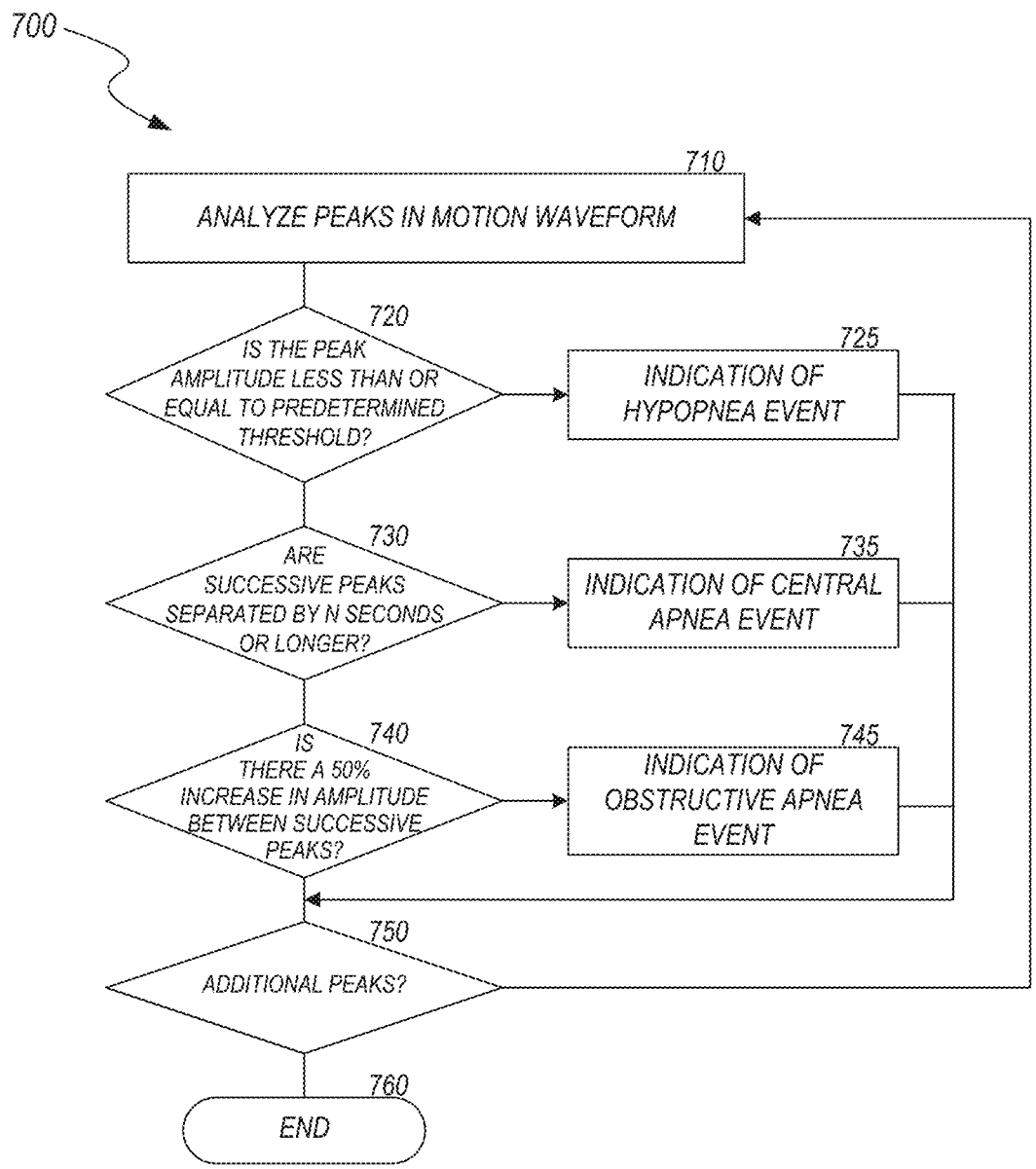
FIG. 7 is a flow diagram of a process configured in accordance with an embodiment of the present technology.

FIG. 7 is a flow diagram of a process 700 configured to identify an apnea event in accordance with an embodiment of the present technology. At block 710, the process analyzes peak in a motion waveform (e.g., the peaks 444 detected in the motion waveform 440 of FIG. 4A). In some embodiments, the process 700 is configured to determine a pose (e.g., supine, prone, non-prone, sitting up, lying down) of the subject corresponding to one or more of the detected peaks. The process 700 can be configured, for example, to monitor a distance (e.g., the distance D of FIG. 1) and/or an orientation between a measurement device (e.g., the device 110 of FIG. 1) and the subject. In certain embodiments, for example, the process 700 can detect one or more aperiodic portions of the motion waveform. The process 700 can associate the one or more detected aperiodic portions of the subject's motion waveform with one or more non-breathing motions (e.g., rolling over, sitting up). If, for example, the subject rolls from one side of her body to another, the resulting motion waveform can arrive from a slightly different distance. By tracking the motion and the distance from which the breathing signal appears, the process 700 can determine an orientation of the subject. The process 700 can be further configured to use the subject's orientation information to detect positional sleep apnea in the subject. In some embodiments, the process 700 can be configured to distinguish between sleep apnea in, for example, a supine position (i.e., the subject lying with her face generally upward or away from a bed), a prone position (i.e., the subject lying with her face generally downward or toward the bed), and/or another position or pose. In some embodiments, the positional information determined by the process 700 at block 710 can be used in subsequent blocks discussed below. In additional embodiments, the process 700 may determine a position or orientation of the subject relative to the measurement device at one or more other blocks of the process 700.

At decision block 720, the process 700 determines whether one or more peaks in the motion waveform are less than a predetermined threshold (e.g., an amplitude 30% less than other peaks in the motion waveform) over a predetermined time duration (e.g., between about 5 s and 60 s, or about 10 s). If the process 700 determines that plurality of peaks are in the motion waveform are less than the predetermined threshold over the predetermined time, the process 700 outputs an indication of a hypopnea event at block 725. Otherwise, the process 700 proceeds to block 730.

At block 730, the process 700 determines whether successive peaks in the motion waveform are separated by a time duration greater than a predetermined threshold time (e.g., 10 seconds). If the process 700 detects successive peaks in the motion waveform separated by the predetermined threshold time or greater, the process 700 outputs an indication of a central apnea event at block 735. Otherwise, the process 700 proceeds to block 740.

At decision block 740, the process 700 determines whether successive peaks in the motion waveform include a first peak and a second, following peak in which the amplitude of the second peak is a predetermined percentage (e.g., 30%, 40%, 50%, 60%, 70%, 80%, 90%, 100% or higher) greater than an amplitude of the first peak. If the process detects successive peaks in the motion waveform in which the second peak has an amplitude greater than the predetermined percentage of the first peak, the process 700 outputs an indication of an obstructive apnea event at block 745. In some embodiments, the process 700 may instead detect a first peak and a second, following peak in which the second peak is a predetermined percentage (e.g., 30%, 40%, 50%, 60%, 70%, 80%, 90%) less than the first peak. At decision block 750, the process 700 determines whether there are additional peaks in the motion waveform. If there are additional peaks in the motion waveform, the process 700 returns to block 710. Otherwise, the process 700 ends at block 760.

Figure 8A:
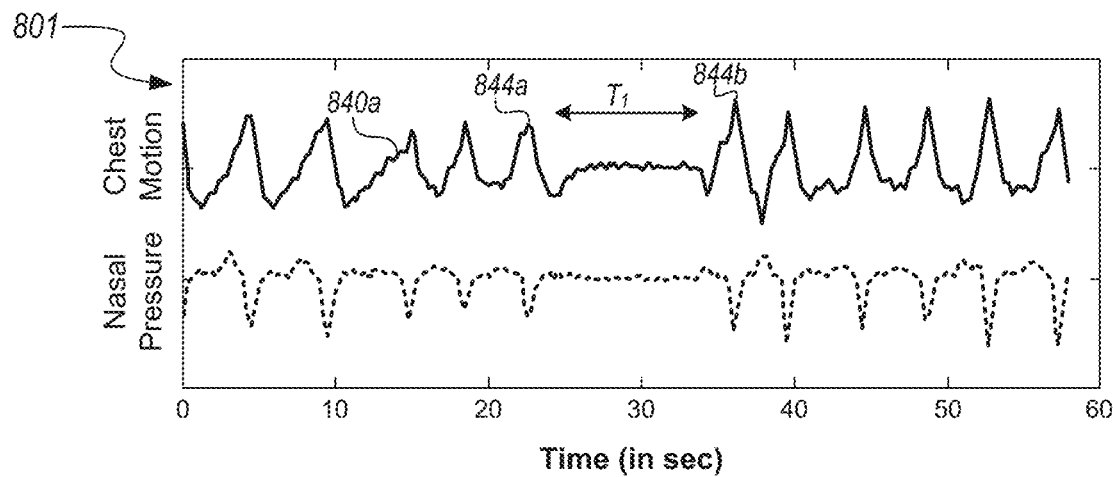
FIGS. 8A-8C are graphs showing examples of apnea and hypopnea events in accordance with an embodiment of the present technology.
Figure 8B:
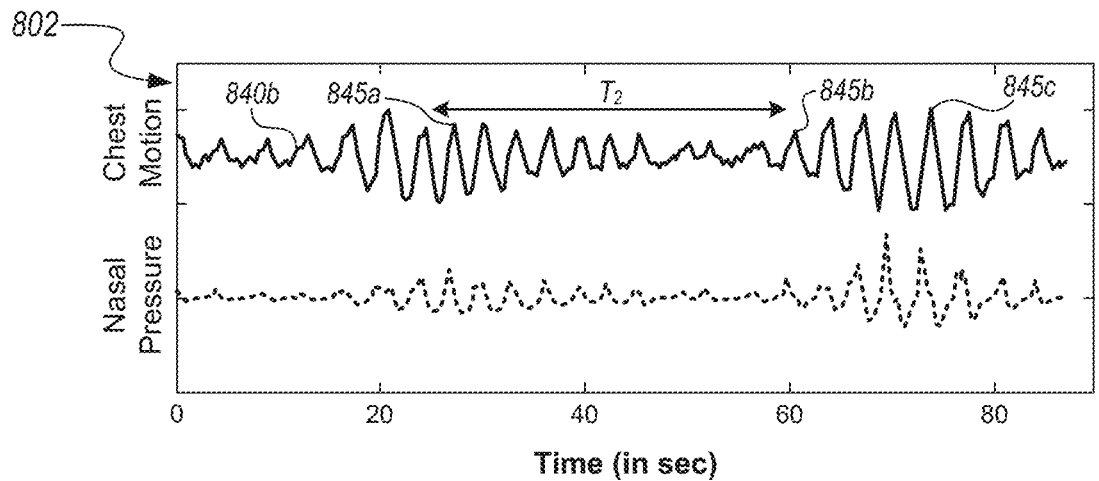
Figure 8C:
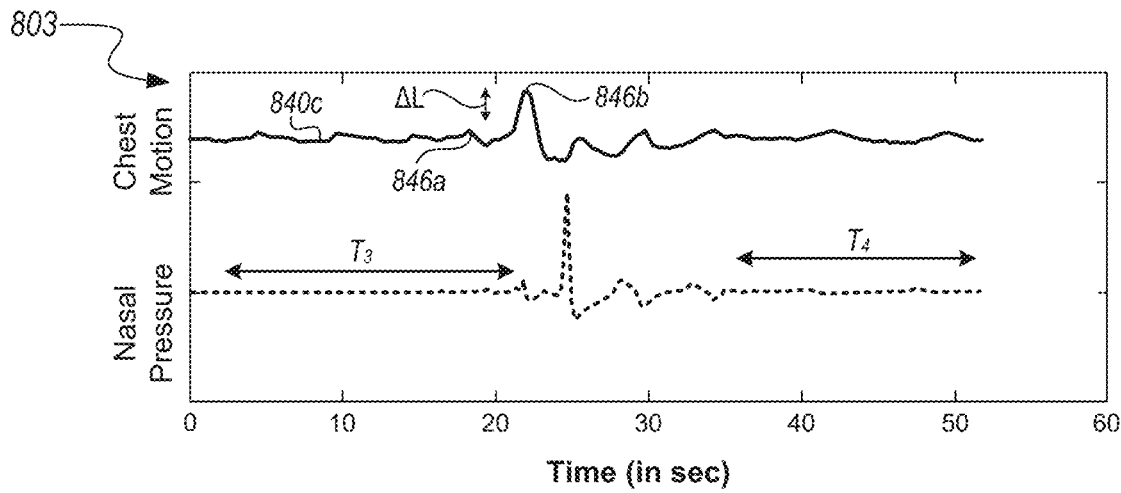

FIGS. 8A-8C show examples of apnea-hypopnea events that may be identified by the process 700 (FIG. 7) in accordance with an embodiment of the present technology. FIG. 8A, for example, is a graph 801 depicting one example of a central apnea event described above with reference to block 730 of FIG. 7. A chest motion waveform 840*a* includes a pair of successive peaks 844*a* and 844*b* separated by time $T_1$ (e.g., about 15 s) greater than a predetermined central apnea threshold time (e.g., about 10 s).

FIG. 8B is a graph 802 depicting one example of hypopnea event described above with reference to block 720 of FIG. 7. A motion waveform 840*b* includes a plurality of peaks, including a first peak 845*a*, a second peak 845*b*, and a third peak 845*c*. The first peak 845*a* and the second peak 845*b* comprise a plurality of peaks in the waveform 840*b* having amplitudes less than a predetermined threshold amplitude (e.g., 30% less than an amplitude of the peak 845*c*) during a predetermined time duration $T_2$ (e.g., about 35 s).

FIG. 8C is a graph 803 depicting one example of an obstructive apnea event described above with reference to block 740 of FIG. 7. A motion waveform 840*c* includes a plurality of peaks, including a first peak 846*a* and, a second peak 846*b*. The second peak 846*b* has an amplitude that is ΔL (e.g., 40%, 50%, 75%) greater than the first peak 846*a* or any other peaks in the waveform 840*c* preceding the second peak 846*b* by a time $T_3$ and/or following the second peak 846*b* by a time $T_4$.

The disclosure may be defined by one or more of the following examples:

1. A method of operating a device to identify sleep apnea events in a subject, the method comprising:
    transmitting sound energy toward the subject using a first transducer on the device, wherein the transducer is configured to generate sound energy over a range of frequencies that includes frequencies less than 20 kHz;
    receiving echoes from the subject corresponding to the transmitted sound energy using a second transducer on the device, wherein the second transducer is configured to produce electrical signals corresponding to the received echoes;
    generating a waveform using the electrical signals; detecting a plurality of peaks in the waveform, wherein individual peaks have a corresponding amplitude and frequency, and further wherein individual peaks are indicative of breathing motion of the subject; and
    outputting an indication of a sleep apnea event for each occurrence of a period of time between successive individual peaks in the waveform exceeding a predetermined threshold time.

2. The method of example 1 wherein transmitting the sound energy comprises emitting a plurality of audio chirps from the first transducer, and wherein individual audio chirps linearly sweep from a first frequency to a second, higher frequency over a predetermined time duration.

3. The method of example 2 wherein the first frequency is about 18 kHz and the second frequency is 20 kHz or greater.

4. The method of examples 2 or 3 wherein at least a portion of the plurality of audio chirps comprise frequency-modulated continuous-wave sound signals emitted from the first transducer.

5. The method of any of examples 2-4 wherein generating the waveform comprises performing a Fourier transform of the emitted audio chirps and the corresponding received echoes over a period of time longer than the predetermined time duration of the individual chirps.

6. The method of example 5 wherein the period of time is approximately 10 times the predetermined time duration of the individual chirps or longer.

7. The method of any of examples 1-6, further comprising repeating the transmitting and receiving for a plurality of transmit/receive cycles, wherein generating the waveform further comprises determining a plurality of frequency shifts between the transmitted sound energy and the corresponding received echoes for each of the plurality of transmit/receive cycles.

8. The method of any of examples 1-7 wherein generating the waveform comprises filtering out signals having a frequency less than about 18 kHz.

9. The method of any of examples 1-8, further comprising outputting an indication of a sleep apnea event for each occurrence of an individual peak in the waveform having an amplitude less than or equal to a predetermined threshold amplitude and time period.

10. The method of example 9, further comprising outputting an indication of a sleep apnea event for each occurrence of an increase of 50% or greater of the amplitudes of successive individual peaks in the waveform.

11. The method of example 10, further comprising outputting the subject's apnea-hypopnea index, wherein outputting the subject's apnea-hypopnea index comprises determining a ratio of a total number of sleep apnea events during a sleep cycle of the subject and a duration of the sleep cycle of the subject.

12. The method of any of examples 1-11 wherein transmitting sound energy comprises transmitting sound energy having a wavelength greater than one half of a distance between the first transducer and the second transducer.

13. A method of operating an electronic device to monitor movements of a subject proximate the electronic device, the method comprising:
    emitting a plurality of audio sweep signals toward the subject from a loudspeaker operatively coupled to the electronic device, wherein individual audio sweep signals linearly sweep from a first frequency less than 20 kHz to a second, higher frequency over a predetermined time duration;
    acquiring audio data at a microphone operatively coupled to the electronic device, wherein the audio data comprises echo signals that correspond to individual audio sweep signals backscattered by the subject toward the microphone;
    processing the emitted audio sweep signals and the acquired audio data to generate a motion waveform; detecting one or more peaks in the motion waveform, wherein individual peaks are indicative of movements of the subject; and outputting an indication of movement of the subject based one or more of the detected peaks.

14. The method of example 13 wherein the first frequency is about 18 kHz and the second frequency is 20 kHz or greater, and further wherein at least portion of the plurality of the audio sweep signals comprise frequency-modulated continuous-wave sound signals.

15. The method of examples 13 or 14 wherein the processing further comprises:
calculating a plurality of frequency domain representations of the emitted audio sweep signals and the echo signals, wherein the frequency domain representations are calculated over a time period lasting a predetermined multiple of the predetermined time duration of the individual audio sweep signals; and
determining a frequency shift in the individual frequency domain representations relative to the first frequency.

16. The method of any of examples 13-15 wherein the individual peaks are indicative of movement of the chest and/or abdomen of the subject, wherein the individual peaks have a corresponding amplitude, and wherein outputting an indication of movement of the subject further comprises outputting an indication of a sleep apnea event for each occurrence of a period of time between successive individual peaks in the motion waveform exceeding a predetermined threshold time.

17. The method of example 16 wherein outputting an indication of movement of the subject further comprises outputting an indication of a sleep apnea event for each occurrence of an individual peak in the waveform having an amplitude less than or equal to a predetermined threshold amplitude.

18. The method of examples 16 or 17 wherein outputting an indication of movement of the subject further comprises outputting an indication of a sleep apnea event for each occurrence of an increase of 50% or greater of the amplitudes of successive individual peaks in the waveform.

19. The method of any of examples 13-18, further comprising:
comparing a frequency of the detected peaks to a predetermined breathing frequency, wherein outputting an indication of movement of the subject comprises outputting an indication of a possible presence of chronic obstructive pulmonary disease in the subject if the frequency of the detected peaks is greater than equal to 115% of the predetermined breathing frequency.

20. A computer program product comprising a non-transitory computer readable storage medium storing computer usable program code executable to perform operations for outputting an indication of a sleep apnea event in a subject, the operations comprising:
transmitting a plurality of chirp signals to a first transducer operatively coupled to a mobile device, wherein individual chirp signals linearly sweep from a first frequency less than 20 kHz to a second, higher frequency over a predetermined time duration;
acquiring echo data from a second transducer operatively coupled to the mobile device, wherein the echo data includes data corresponding to individual chirp signals reflected by the subject toward the second transducer;
demodulating the acquired echo data to obtain a motion signal indicative of respiratory motion of the subject;
detecting one or more amplitude peaks in the motion signal; and
outputting an indication of a sleep apnea event if a period of time between successive individual amplitude peaks in the motion signal exceeds a predetermined threshold time.

21. The computer program product of example 20 wherein the operations further comprise repeating the transmitting and acquiring for a predetermined number of transmit/acquisition cycles, wherein demodulating the acquired echo data comprises performing a single Fourier transform of the predetermined number of transmit/acquisition cycles.

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments applicable to a wide range of human physiological behaviors and illnesses.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Where the context permits, singular or plural terms may also include the plural or singular term, respectively. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A non-transitory computer-readable storage medium storing instructions that, when executed by a computing system, cause the computing system to perform operations comprising:
emitting audio sweep signals, from an electronic device, toward an abdomen or chest of a subject spaced apart from and out of contact with the electronic device,
wherein individual audio sweep signals linearly sweep from a first frequency less than 20 kHz to a second, higher frequency over a predetermined time duration;
acquiring echo data from a microphone operatively coupled to the electronic device, wherein the echo data includes data corresponding to individual audio sweep signals reflected by the subject toward the microphone;
demodulating the acquired echo data to obtain a motion signal indicative of respiratory motion of the subject;
detecting one or more amplitude peaks in the motion signal; and
outputting an indication of movement of the abdomen or chest of the subject based one or more of the detected peaks, wherein the indication of movement is associated with one or more medical conditions of the subject.

2. The non-transitory computer-readable storage medium of claim 1 wherein the operations further comprise:
repeating the emitting and acquiring for a predetermined number of emission/acquisition cycles,
wherein demodulating the acquired echo data comprises performing a single frequency transform of the echo data received during the predetermined number of emission/acquisition cycles.

3. The non-transitory computer-readable storage medium of claim 1 wherein the first frequency is about 18 kHz and the second frequency is 20 kHz or greater.

4. The non-transitory computer-readable storage medium of claim 1 wherein at least a portion of the audio sweep signals comprise frequency-modulated continuous-wave sound signals emitted from a transducer operatively coupled to the electronic device.

5. The non-transitory computer-readable storage medium of claim 1 wherein the indication of movement is associated with an obstructive apnea event in the subject.

6. The non-transitory computer-readable storage medium of claim 1 wherein the indication of movement is associated with a sleep apnea event in the subject.

7. The non-transitory computer-readable storage medium of claim 1 wherein outputting an indication of movement of the abdomen or chest of the subject further comprises outputting an indication of a sleep apnea event for each occurrence of an increase of 50% or greater of the amplitudes of successive individual peaks in the waveform.

8. The non-transitory computer-readable storage medium of claim 1 wherein the indication of movement is associated with chronic obstructive pulmonary disease (COPD) in the subject.

9. A method of operating an electronic device to monitor movements of a subject spaced apart from and out of contact with the electronic device, the method comprising:
transmitting sound energy toward the subject using a first transducer operatively coupled to the electronic device, wherein transmitting the sound energy comprises emitting a plurality of audio chirps from the first transducer, and wherein individual audio chirps linearly sweep from a first frequency to a second, higher frequency over a predetermined time duration, and further wherein the first transducer is configured to generate sound energy over a range of frequencies that includes frequencies less than 20 kHz;
receiving echoes from the subject corresponding to the transmitted sound energy using a second transducer operatively coupled to the electronic device, wherein the second transducer is configured to produce electrical signals corresponding to the received echoes;
generating a waveform using the electrical signals; and
detecting a plurality of peaks in the waveform, wherein individual peaks have a corresponding amplitude, and further wherein individual peaks are indicative of breathing motion of the subject.

10. The method of claim 9 wherein the first frequency is about 18 kHz and the second frequency is 20 kHz or greater.

11. The method of claim 9 wherein at least portion of the plurality of audio chirps comprise frequency-modulated continuous-wave sound signals emitted from the first transducer.

12. The method of claim 9 wherein generating the waveform comprises performing a Fourier transform of the electrical signals corresponding to the received echoes over a period of time longer than the predetermined time duration of the individual chirps.

13. The method of claim 12 wherein the period of time is approximately 10 times the predetermined time duration of the individual chirps or longer.

14. The method of claim 9 wherein transmitting sound energy comprises transmitting sound energy having a wavelength greater than one half of a distance between the first transducer and the second transducer.

15. The method of claim 9, further comprising repeating the transmitting and receiving for a plurality of transmit/receive cycles, wherein generating the waveform further comprises determining a plurality of frequency shifts between the transmitted sound energy and the corresponding received echoes for each of the plurality of transmit/receive cycles.

16. The method of claim 9 wherein generating the waveform comprises filtering out signals having a frequency less than about 18 kHz.

17. The method of claim 9, further comprising outputting an indication of a sleep apnea event for each occurrence of an individual peak in the waveform having an amplitude less than or equal to a predetermined threshold amplitude.

18. The method of claim 17, further comprising outputting an indication of the sleep apnea event for each occurrence of an increase of 50% or greater of the amplitudes of successive individual peaks in the waveform.

19. The method of claim 16, further comprising outputting the subject's apnea-hypopnea index, wherein outputting the subject's apnea-hypopnea index comprises determining a ratio of a total number of sleep apnea events during a sleep cycle of the subject and a duration of the sleep cycle of the subject.

* * * * *